United States Patent
Dumesic et al.

(10) Patent No.: US 10,207,960 B2
(45) Date of Patent: Feb. 19, 2019

(54) SELECTIVE CATALYTIC PRODUCTION OF LINEAR ALPHA OLEFINS FROM LACTONES AND UNSATURATED CARBOXYLIC ACIDS

(71) Applicant: Wisconsin Alumni Research Foundation, Madison, WI (US)

(72) Inventors: James Anthony Dumesic, Verona, WI (US); Dong Wang, Madison, WI (US); Sikander Hussain Hakim, Madison, WI (US); David Martin Alonso, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 875 days.

(21) Appl. No.: 13/928,811

(22) Filed: Jun. 27, 2013

(65) Prior Publication Data
US 2015/0005558 A1  Jan. 1, 2015

(51) Int. Cl.
*C07C 1/00* (2006.01)
*C07C 1/207* (2006.01)

(52) U.S. Cl.
CPC ........ *C07C 1/2078* (2013.01); *C07C 2521/04* (2013.01); *C07C 2521/12* (2013.01); *C07C 2523/30* (2013.01)

(58) Field of Classification Search
CPC ... C07C 1/20; C07C 2529/85; C07C 2529/40; C07C 1/22; C07C 1/2078; B01J 29/85; C10G 3/00
USPC ................ 585/640, 324, 251, 242, 638, 500
See application file for complete search history.

(56) References Cited

U.S. PATENT DOCUMENTS

| | | | |
|---|---|---|---|
| 4,996,384 A * | 2/1991 | Pelrine et al. ............... | 585/530 |
| 5,004,815 A | 4/1991 | Danheiser et al. | |
| 5,164,497 A * | 11/1992 | King ...................... | B01J 21/02 544/177 |
| 8,003,818 B2 | 8/2011 | Van Den Brink et al. | |
| 8,410,326 B2 * | 4/2013 | Dumesic et al. ............ | 585/327 |
| 2010/0312028 A1 | 12/2010 | Olson et al. | |
| 2011/0172476 A1* | 7/2011 | Dumesic et al. ............ | 585/324 |
| 2012/0035403 A1* | 2/2012 | Flytzani-Stephanopoulos ........... | C07C 1/2078 585/240 |

OTHER PUBLICATIONS

Levin, I.; Brandon, D. "Metastable Alumina Polymorphs: Crystal Structures and Transition Sequences". J. Am. Ceram. Soc., 81, (1998). pp. 1995-2012.*

(Continued)

*Primary Examiner* — In Suk C Bullock
*Assistant Examiner* — Aaron W Pierpont
(74) *Attorney, Agent, or Firm* — Joseph T. Leone, Esq.; DeWitt LLP

(57) ABSTRACT

Described is a method to make linear alpha olefins. The method includes the steps of contacting a feedstock having a lactone and/or an unsaturated carboxylic acid with a solid acid catalyst having acidic catalytic sites including Lewis acid catalytic sites, for a time and a temperature wherein at least a fraction of the lactone and/or unsaturated carboxylic acid present in the feedstock is converted into a linear alpha olefin. The method may optionally take place in the presence of water. The solid acid catalyst should preferably have at least 50% Lewis acid catalytic sites.

34 Claims, 1 Drawing Sheet

(56) References Cited

OTHER PUBLICATIONS

Bardin et al. (1998) Acidity of Keggin-Type Heteropolycompounds Evaluated by Catalytic Probe Reactions, Sorption Microcalorimetry and Density Functional Quantum Chemical Calculations, *J. of Physical Chemistry B*, 102:10817-10825.

Bond, J.Q. et al., Integrated Catalytic Conversion of γ-Valerolactone to Liquid Alkenes for Transportation Fuels, *Science*, 2010, 327, 1110-1114.

Bond, J.Q. et al., γ-Valerolactone Ring-Opening and Decarboxylation over $SiO_2/Al_2O_3$ in the Presence of Water, *Langmuir*, 2010, 26, 16291-16298.

Bond, J.Q. et al., Interconversion between γ-valerolactone and pentenoic acid combined with decarboxylation to form butane over silica/alumnia, *J. Catal.*, 2011, 281, 290-299.

Corma, A., Inorganic Solid Acids and Their Use in Acid-Catalyzed Hydrocarbon Reactions, *Chem. Rev.*(Washington, DC, U. S.), 1995, 95, 559-614.

Emeis, C.A., Determination of Integrated Molar Extinction Coefficients for Infrared Absorption Bands of Pyridine Adsorbed on Solid Acid Catalysts, *J. Catal.* 1993, 141, 347-354.

Gielgens, L. H. et al., Skeletal Isomerisation of 1-Butene on Tungsten Oxide Catalysts, *J. Catal.*, 1995, 154, 201-207.

Kraus, G.A. et al., A Large-Scale Synthesis of α-Olefins and α, ω-Dienes, *Synthesis*, 2012, 44, 3003-3005.

Mahrwald, R., vol. 1: Enolates, Organocatalysis, Biocatalysis and Natural Product Synthesis, *Modern Aldol Reactions*, WILEY-VCH 2004.

Nexant Chemical Systems, *Alpha Olefins(02/03-4) PERP Report*, 2004.

Nikolau, B.J. et al., Platform biochemical for a biorenewable chemical industry, *The Plant Journal*, 2008, 54, 536-545.

Shanks, B.H., Unleashing Biocatalysis/Chemical Catalysis Synergies for Efficient Biomass Conversion, *ACS Chem. Biol.*, 2007, 2, 533-535.

Soled, S.L. et al., Comparison of the Acidities of $WO_3/Al_2O_3$ and Ultrastable Faujasite Catalysts. *J. Catal.*, 1988, 111, 286-295.

Van Der Klis, F. et al., Renewable linear alpha olefins by selective ethenolysis of decarboxylated unsaturated fatty acids, *Eur. J. Lipid Sci. Technol.*, 2012, 114, 911-918.

Voge, H.H., Isomerization Equilibria among the n-Butenes, *J. Am. Chem. Soc.*, 1946, 68, 550-553.

Vogt, D., Oligomerization of Ethylene to Higher Linear α-Olefins, *Applied Homogeneous Catalysis With Organometallic Compounds* 1996, vol. 1, pp. 245-258.

Weissermel, K., *Industrial Organic Chemistry*, 1997 (Book—Copy not provided).

Roman-Leshkov, Y., et al., Activation of Carbonyl-Containing Molecules with Solid Lewis Acids in Aqueous Media, *ACS Catal.*, 2011, 1, 1566-1580.

Wang, D., et al., A highly selective route to linear alpha olefins from biomass-derived lactones and unsaturated acids, *Chem. Commun.*, 2013, 49, 7040-7042.

\* cited by examiner

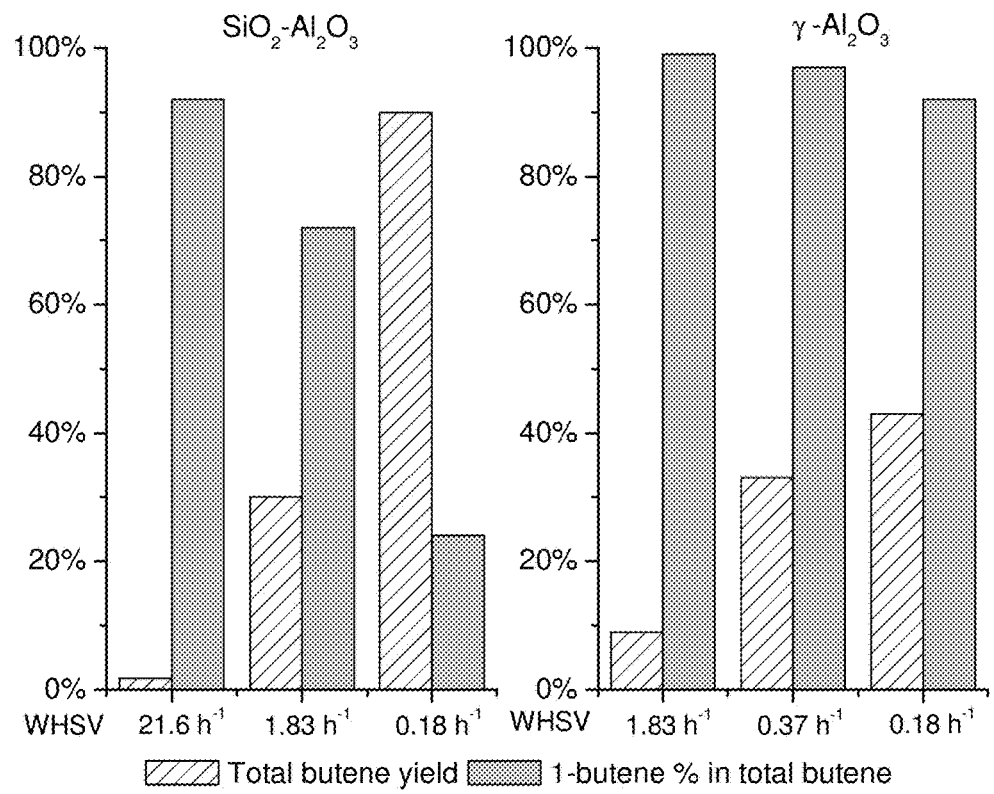
FIG. 1  FIG. 2

SELECTIVE CATALYTIC PRODUCTION OF LINEAR ALPHA OLEFINS FROM LACTONES AND UNSATURATED CARBOXYLIC ACIDS

STATEMENT REGARDING FEDERALLY SPONSORED RESEARCH OR DEVELOPMENT

This invention was made with government support under DE-FCO2-07ER64494 awarded by the US Department of Energy and 0813570 awarded by the National Science Foundation. The government has certain rights in the invention.

CROSS-REFERENCE TO RELATED APPLICATIONS

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

Field of the Invention

Disclosed herein is a method to make linear alpha-olefins.

Description of Related Art Including Information Disclosed Under 37 CFR 1.97 and 1.98

The use of biomass feedstocks is central to satisfy the long-term need for carbon-based commodity chemicals in a sustainable manner. A promising strategy for converting biomass-derived carbohydrates to value-added chemicals is to take advantage of synergies between the high chemo- and stereo-selectivity of biocatalysis and the high efficiency of chemical catalysis. B. H. Shanks, *ACS Chem. Biol.,* 2007, 2, 533-535. An example is polyketide/fatty acid biosynthesis, which offers flexibility to produce targeted molecules with specified carbon chain lengths and functionalities within a homologous series based on a single metabolic pathway. B. J. Nikolau, M. A. D. N. Perera, L. Brachova and B. Shanks, *The Plant Journal,* 2008, 54, 536-545. The products assembled through this route create a diverse platform, which can subsequently be upgraded by chemical catalysis to access families of commodity chemicals.

Linear alpha olefins (LAOs) are valuable commodity chemicals featuring highly accessible terminal double bonds. LAOs are versatile building blocks for making a broad range of chemical products. D. Vogt, in *Applied Homogeneous Catalysis With Organometallic Compounds* 1996, vol. 1, pp. 245-258. Short-chain LAOs ($C_4$-$C_8$) are used as co-monomers for producing high-density polyethylene (HDPE) and linear low-density polyethylene (LLDPE). Longer chain-length LAOs are used as precursors to detergents ($C_{12}$-$C_{14}$), synthetic oils and plasticizers ($C_6$-$C_{10}$), and specialty chemicals such as oilfield fluids ($C_{16}$-$C_{18}$). Id. The linearity of LAOs leads to products with desirable mechanical properties, such as increased flexibility, and strength, and advantages such as biodegradability. K. Weissermel and H.-J. Arpe, *Industrial Organic Chemistry,* 1997. The annual global demand for LAO ($C_4$-$C_{20+}$) was approximately 3.4 million metric tons at the end of 2002 and has been growing rapidly. *Alpha Olefins*(02/03-4) *PERP Report, Nexant Chemical Systems,* 2004.

The production of LAOs is inherently challenging due to the ease of migration of the terminal double bond to internal positions. LAOs are conventionally manufactured from fossil fuel feedstocks by two main routes, oligomerization of ethylene and cracking of Fischer-Tropsch products. K. Weissermel and H.-J. Arpe, *Industrial Organic Chemistry,* 1997. These processes necessarily lead to a distribution of LAOs with different chain lengths. Moreover, LAOs with odd carbon numbers cannot be produced by direct ethylene oligomerization. In addition, current processes overwhelmingly rely on fossil carbon and thus are not sustainable. In this regard, the development of a process to produce LAOs from renewable feedstocks has become of wide interest. For instance, a process has been demonstrated for LAO production by decarbonylation/dehydration of fatty acids over homogenous catalysts based on Pd. G. A. Kraus and S. Riley, *Synthesis,* 2012, 44, 3003-3005. Another process involves silver (II) mediated decarboxylation of fatty acids followed by ethenolysis over a commercial metathesis catalyst to produce renewable LAOs. F. van der Klis, J. Le Notre, R. Blaauw, J. van Haveren and D. S. van-Es, *Eur. J. Lipid Sci. Technol.,* 2012, 114, 911-918. However, these processes require using expensive homogeneous catalysts. Not only are the catalysts prohibitively expensive, because they are homogeneous, they are difficult to separate and recycle from the product stream. Thus there remains a long-felt and unmet need to produce LAOs cheaply and from renewable feedstocks.

BRIEF SUMMARY OF THE INVENTION

Disclosed herein is a process to convert hydroxy carboxylic acids, unsaturated carboxylic acids and lactones ($C_n$) obtained from renewable sources such as biomass to produce linear alpha olefins (LAOs) ($C_{n-1}$) by selective decarboxylation. The method uses inexpensive, robust heterogeneous solid acid catalysts, and can use as a feedstock a wide range of hydroxy carboxylic acids, unsaturated carboxylic acids and their lactones. Unsaturated carboxylic acids are made easily by dehydrating hydroxy carboxylic acids over acid catalysts. Thus, the process disclosed herein is equally applicable to hydroxy carboxylic acids, which can be dehydrated to unsaturated carboxylic acids, and then converted by the process described herein into LAOs. Similarly, hydroxy carboxylic acids are also converted easily to lactones by dehydration over acid catalysts. The lactones can then be converted to LAOs using the process described herein. Any substituted or unsubstituted organic compound with a carboxylic acid functionality or a derivative thereof (such as corresponding esters) that can readily produce an unsaturated carboxylic acid are suitable for the current process.

Disclosed herein is a method to make linear alpha olefins. The method comprises contacting a feedstock comprising at least one lactone, at least one unsaturated carboxylic acid, or a combination of at least one lactone and at least one unsaturated carboxylic acid with a solid acid catalyst having acidic catalytic sites including Lewis acid catalytic sites, for a time and a temperature wherein at least a fraction of the lactone or unsaturated carboxylic acid present in the feedstock is converted into a linear alpha olefin. In all of the embodiments of the process described herein, the reaction may be carried out in the presence or in the absence of a co-fed solvent (i.e., a co-solvent), such as water, alcohols (methanol, ethanol, propanol, etc), ethers (dimethyl ether, diethyl ether, etc.), ketones (acetone, methyl-ethyl ketone, etc.), aldehydes (formaldehyde, acetaldehyde, etc.), and the like. It is generally preferred, although not required, to run the reaction in the presence of a co-solvent and the preferred co-solvent is water.

Generally speaking at least 50%, at least 60%, at least 70%, at least 80%, or at least 90% of the acidic catalytic sites on the solid acid catalyst should be Lewis acid catalytic sites. Percentages below this are within the scope of the invention, but are less preferred. It is preferred that the process yields at least 70%, or at least 75%, or at least 80%, or at least 85%, or at least 90% alpha olefins as a percentage of all olefins (alpha olefins and internal olefins) produced by the process.

The reaction may be conducted by contacting the feedstock with the solid acid catalyst at a temperature of from about 500 K to about 1000 K, or from about 600 K to about 900 K, or from about 625 K to about 850 K, or from about 650 K to about 800 K.

The solid acid catalyst may comprise a metal selected from the group consisting of transition metals, lanthanide metals, and metals from Groups 13, 14 and 15 of the periodic table of the elements. The solid acid catalyst may comprise aluminum, such as $\gamma$-$Al_2O_3$.

BRIEF DESCRIPTION OF THE SEVERAL VIEWS OF THE DRAWINGS

FIG. 1 is a histogram showing butene production by decarboxylation of gamma valerolactone (GVL) over $SiO_2$—$Al_2O_3$ catalyst; 30 wt % GVL in water, 648 K, 1 bar.

FIG. 2 is a histogram showing butene production by decarboxylation of GVL over $\gamma$-$Al_2O_3$ catalyst; 30 wt % GVL in water, 648 K, 1 bar.

DETAILED DESCRIPTION OF THE INVENTION

Abbreviations and Definitions

"Biomass" as used herein includes materials containing cellulose, hemicellulose, lignin, protein and carbohydrates such as starch and sugar. Common forms of biomass include trees, shrubs and grasses, corn and corn husks as well as municipal solid waste, waste paper and yard waste. Biomass high in starch, sugar or protein such as corn, grains, fruits and vegetables, is usually consumed as food. Conversely, biomass high in cellulose, hemicellulose and lignin is not readily digestible by humans and is primarily utilized for wood and paper products, fuel, or is discarded as waste. "Biomass" as used herein explicitly includes branches, bushes, canes, corn and corn husks, energy crops, forests, fruits, flowers, grains, grasses, herbaceous crops, leaves, bark, needles, logs, roots, saplings, short rotation woody crops, shrubs, switch grasses, trees, vegetables, vines, hard and soft woods. In addition, biomass includes organic waste materials generated from agricultural processes including farming and forestry activities, specifically including forestry wood waste. "Biomass" includes virgin biomass and/or non-virgin biomass such as agricultural biomass, commercial organics, construction and demolition debris, municipal solid waste, waste paper, and yard waste. Municipal solid waste generally includes garbage, trash, rubbish, refuse and offal that is normally disposed of by the occupants of residential dwelling units and by business, industrial and commercial establishments, including but not limited to: paper and cardboard, plastics, food scraps, scrap wood, saw dust, and the like.

"Biomass-derived"=Compounds or compositions fabricated or purified from biomass.

"Carbohydrate" is defined herein as a compound that consists only of carbon, hydrogen, and oxygen atoms, in any ratio.

"Cellulose" refers to a polysaccharide of glucose monomers $((C_6H_{10}O_5)_n)$; "cellulosic biomass" refers to biomass as described earlier that comprises cellulose, and/or consists essentially of cellulose, and/or consists entirely of cellulose. Lignocellulosic biomass refers to biomass comprising cellulose, hemicellulose, and lignin. Lignocellulosic biomass comprises xylose, as does hemicellulose.

"Heteropolyacid"=A class of solid-phase acids exemplified by such species as $H_4SiW_{12}O_{40}$, $H_3PW_{12}O_{40}$, $H_6P_2W_{18}O_{62}$, $H_{3+x}PMo_{12-x}V_xO_{40}$ and the like. Heteropolyacids are solid-phase acids having a well-defined local structure, the most common of which is the tungsten-based Keggin structure. The Keggin unit comprises a central $PO_4$ tetrahedron, surrounded by 12 $WO_6$ octahedra. The standard unit has a net charge (−3), and thus requires three cations to satisfy electroneutrality. If the cations are protons, the material functions as a Brønsted acid. The acidity of these compounds (as well as other physical characteristics) can be "tuned" by substituting different metals in place of tungsten in the Keggin structure. See, for example, Bardin et al. (1998) "Acidity of Keggin-Type Heteropolycompounds Evaluated by Catalytic Probe Reactions, Sorption Microcalorimetry and Density Functional Quantum Chemical Calculations," *J. of Physical Chemistry B*, 102:10817-10825.

"Homogeneous catalyst"=A catalyst that exists in the same phase (solid, liquid, or gas) as the reactants under reaction conditions.

"Heterogeneous catalyst"=A catalyst that exists in a different phase than the reactants under reaction conditions.

"Lactone" as used herein refers to an unsubstituted or substituted cyclic ester, having a single oxygen heteroatom in the ring, and having from four to six total atoms in the ring—i.e., beta, gamma, and delta lactones, derived from any corresponding $C_4$ to $C_{16}$ carboxylic acid. Thus, as used herein, the term "lactone" explicitly includes (without limitation) unsubstituted and substituted beta- and gamma-butyrolactone and beta-, gamma-, and delta-valerolactones to beta-, gamma, and delta-hexadecalactones. Some lactones are miscible in water, such as GVL; other lactones have more limited solubility in water. Gamma- and delta-lactones are preferred. Gamma-valerolactone is most preferred.

Lewis Acid/Base=A Lewis acid is defined herein as any chemical species that is an electron-pair acceptor, i.e., any chemical species that is capable of receiving an electron pair, without limitation. A Lewis base is defined herein as any chemical species that is an electron-pair donor, that is, any chemical species that is capable of donating an electron pair, without limitation.

In preferred versions of the invention, the Lewis acid (also referred to as the Lewis acid catalyst) may be any Lewis acid based on transition metals, lanthanide metals, and metals from Groups 13, 14 and 15 of the periodic table of the elements, including boron, aluminum, gallium, indium, titanium, zirconium, tin, vanadium, arsenic, antimony, bismuth, lanthanum, dysprosium, and ytterbium. One skilled in the art will recognize that some elements are better suited in the practice of the method. Illustrative examples include $AlCl_3$, (alkyl)$AlCl_2$, $(C_2H_5)_2AlCl$, $(C_2H_5)_3Al_2Cl_3$, $BF_3$, $SnCl_4$ and $TiCl_4$.

The Group 4, 5 and 14 Lewis acids generally are designated by the formula $MX_4$; wherein M is Group 4, 5, or 14 metal, and X is a halogen independently selected from the group consisting of fluorine, chlorine, bromine, and iodine, preferably chlorine. X may also be a pseudohalogen. Non-limiting examples include titanium tetrachloride, titanium tetrabromide, vanadium tetrachloride, tin tetrachloride and zirconium tetrachloride. The Group 4, 5, or 14 Lewis acids may also contain more than one type of halogen. Non-limiting examples include titanium bromide trichloride, titanium dibromide dichloride, vanadium bromide trichloride, and tin chloride trifluoride.

Group 4, 5 and 14 Lewis acids useful in the method may also have the general formula $MR_nX_{4-n}$; wherein M is Group 4, 5, or 14 metal; wherein R is a monovalent hydrocarbon radical selected from the group consisting of $C_1$ to $C_{12}$ alkyl, aryl, arylalkyl, alkylaryl and cycloalkyl radicals; wherein n is an integer from 0 to 4; and wherein X is a halogen independently selected from the group consisting of fluorine, chlorine, bromine, and iodine, preferably chlorine. X may also be a pseudohalogen. Non-limiting examples include benzyltitanium trichloride, dibenzyltitanium dichloride, benzylzirconium trichloride, dibenzylzirconium dibromide, methyltitanium trichloride, dimethyltitanium difluoride, dimethyltin dichloride and phenylvanadium trichloride.

Group 4, 5 and 14 Lewis acids useful in method may also have the general formula $M(RO)_nR'_mX_{(m+n)}$; wherein M is Group 4, 5, or 14 metal; RO is a monovalent hydrocarboxy radical selected from the group consisting of $C_1$ to $C_{30}$ alkoxy, aryloxy, arylalkoxy, alkylaryloxy radicals; R' is a monovalent hydrocarbon radical selected from the group consisting of $C_1$ to $C_{12}$ alkyl, aryl, arylalkyl, alkylaryl and cycloalkyl radicals; n is an integer from 0 to 4; m is an integer from 0 to 4 such that the sum of n and m is not more than 4; and X is a halogen independently selected from the group consisting of fluorine, chlorine, bromine, and iodine, preferably chlorine. X may also be a pseudohalogen. Non-limiting examples include methoxytitanium trichloride, n-butoxytitanium trichloride, di(isopropoxy)titanium dichloride, phenoxytitanium tribromide, phenylmethoxyzirconium trifluoride, methyl methoxytitanium dichloride, methyl methoxytin dichloride and benzyl isopropoxyvanadium dichloride.

Group 5 Lewis acids may also have the general formula $MOX_3$; wherein M is a Group 5 metal; X is a halogen independently selected from the group consisting of fluorine, chlorine, bromine, and iodine, preferably chlorine. A non-limiting example is vanadium oxytrichloride.

The Group 13 Lewis acids have the general formula $MX_3$; wherein M is a Group 13 metal and X is a halogen independently selected from the group consisting of fluorine, chlorine, bromine, and iodine, preferably chlorine. X may also be a pseudohalogen. Non-limiting examples include aluminum trichloride, boron trifluoride, gallium trichloride, indium trifluoride, and the like.

The Group 13 Lewis acids useful in method may also have the general formula: $MR_nX_{3-n}$ wherein M is a Group 13 metal; R is a monovalent hydrocarbon radical selected from the group consisting of $C_1$ to $C_{12}$ alkyl, aryl, arylalkyl, alkylaryl and cycloalkyl radicals; and n is an number from 0 to 3; and X is a halogen independently selected from the group consisting of fluorine, chlorine, bromine, and iodine, preferably chlorine. X may also be a pseudohalogen. Non-limiting examples include ethylaluminum dichloride, methylaluminum dichloride, benzylaluminum dichloride, isobutylgallium dichloride, diethylaluminum chloride, dimethylaluminum chloride, ethylaluminum sesquichloride, methylaluminum sesquichloride, trimethylaluminum and triethylaluminum.

Group 13 Lewis acids useful in this disclosure may also have the general formula $M(RO)_nR'_mX_{3-(m+n)}$; wherein M is a Group 13 metal; RO is a monovalent hydrocarboxy radical selected from the group consisting of $C_1$ to $C_{30}$ alkoxy, aryloxy, arylalkoxy, alkylaryloxy radicals; R' is a monovalent hydrocarbon radical selected from the group consisting of $C_1$ to $C_{12}$ alkyl, aryl, arylalkyl, alkylaryl and cycloalkyl radicals; n is a number from 0 to 3; m is an number from 0 to 3 such that the sum of n and m is not more than 3; and X is a halogen independently selected from the group consisting of fluorine, chlorine, bromine, and iodine, preferably chlorine. X may also be a pseudohalogen. Non-limiting examples include methoxyaluminum dichloride, ethoxyaluminum dichloride, 2,6-di-tert-butylphenoxyaluminum dichloride, methoxy methylaluminum chloride, 2,6-di-tert-butylphenoxy methylaluminum chloride, isopropoxygallium dichloride and phenoxy methylindium fluoride.

Group 13 Lewis acids useful in this disclosure may also have the general formula $M(RC(O)O)_nR'_mX_{3-(m+n)}$; wherein M is a Group 13 metal; RC(O)O is a monovalent hydrocarbacyl radical selected from the group consisting of $C_2$ to $C_{30}$ alkacyloxy, arylacyloxy, arylalkylacyloxy, alkylarylacyloxy radicals; R' is a monovalent hydrocarbon radical selected from the group consisting of $C_1$ to $C_{12}$ alkyl, aryl, arylalkyl, alkylaryl and cycloalkyl radicals; n is a number from 0 to 3 and m is a number from 0 to 3 such that the sum of n and m is not more than 3; and X is a halogen independently selected from the group consisting of fluorine, chlorine, bromine, and iodine, preferably chlorine. X may also be a pseudohalogen. Non-limiting examples include acetoxyaluminum dichloride, benzoyloxyaluminum dibromide, benzoyloxygallium difluoride, methyl acetoxyaluminum chloride, and isopropoyloxyindium trichloride.

The most preferred Lewis acids for use in the method are metal halides generally and more specifically transition metal halides, lanthanide metal halides, and Group 13 and 14 metal halides. Preferred among the metal halides are metal chlorides. Preferred transition metal chlorides include, but are not limited to, $TiCl_4$, $VCl_3$. and the like. Preferred Group 13 and 14 metal halides and chlorides include, but are not limited to, $BF_3$, $AlCl_3$, $SnCl_4$, $InCl_3$, and $GaCl_3$. Preferred lanthanide chlorides include, but are not limited to, $LaCl_3$, $DyCl_3$ and $YbCl_3$.

A "solid acid catalyst" can comprise one or more solid acid materials. The solid acid catalyst can be used independently or alternatively can be utilized in combination with one or more mineral acid or other types of catalysts. Exemplary solid acid catalysts which can be utilized include, but are not limited to, heteropoly acids, acid resin-type catalysts, meso-porous silicas, acid clays, sulfated zirconia, molecular sieve materials, zeolites, and acidic material on a thermo-stable support. Where an acidic material is provided on a thermo-stable support, the thermo-stable support can include for example, one or more of silica, tin oxide, niobia, zirconia, titania, carbon, alpha-alumina, and the like. The oxides themselves (e.g., $ZrO_2$, $SnO_2$, $TiO_2$, etc.) which may optionally be doped with additional acid groups such as $SO_4$ may also be used as solid acid catalysts.

Further examples of solid acid catalysts include strongly acidic ion exchangers such as cross-linked polystyrene containing sulfonic acid groups. For example, the Amberlyst®-brand resins are functionalized styrene-divinylbenzene copolymers with different surface properties and porosities. The functional group is generally of the sulfonic acid type. The Amberlyst®-brand resins are supplied as gellular or macro-reticular spherical beads. (Amberlyst® is a registered trademark of the Dow Chemical Co.) Similarly, Nafion®-brand resins are sulfonated tetrafluoroethylene-based fluoropolymer-copolymers which are solid acid catalysts. Nafion® is a registered trademark of E.I. du Pont de Nemours & Co.)

Zeolites may also be used as solid acid catalysts. Of these, H-type zeolites are generally preferred, for example zeolites in the mordenite group or fine-pored zeolites such as zeolites X, Y and L, e.g., mordenite, erionite, chabazite, or faujasite. Also suitable are ultrastable zeolites in the faujasite group which have been dealuminated.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, 5, 6, from 1 to 9, from 3.6 to 4.6, from 3.5 to 9.9, and so forth.

All references to singular characteristics or limitations shall include the corresponding plural characteristic or limitation, and vice-versa, unless otherwise specified or clearly implied to the contrary by the context in which the reference is made.

The processes described herein can be run in batch mode, semi-continuous mode, and/or continuous mode, all of which are explicitly included herein.

All combinations of method or process steps as used herein can be performed in any order, unless otherwise specified or clearly implied to the contrary by the context in which the referenced combination is made.

The methods described and claimed herein can comprise, consist of, or consist essentially of the essential elements and limitations of the disclosed methods, as well as any additional or optional ingredients, components, or limitations described herein or otherwise useful in synthetic organic chemistry and chemical engineering.

The Process:

When a solution of a lactone, such as γ-valerolactone (GVL) is reacted over a solid acid catalyst such as silica-alumina ($SiO_2$—$Al_2O_3$) at temperatures near 648 K, the lactone reactant undergoes ring-opening to produce 3- and 4-pentenoic acids (in the case of GVL), which then isomerize to 2-pentenoic acid. See Scheme 1.

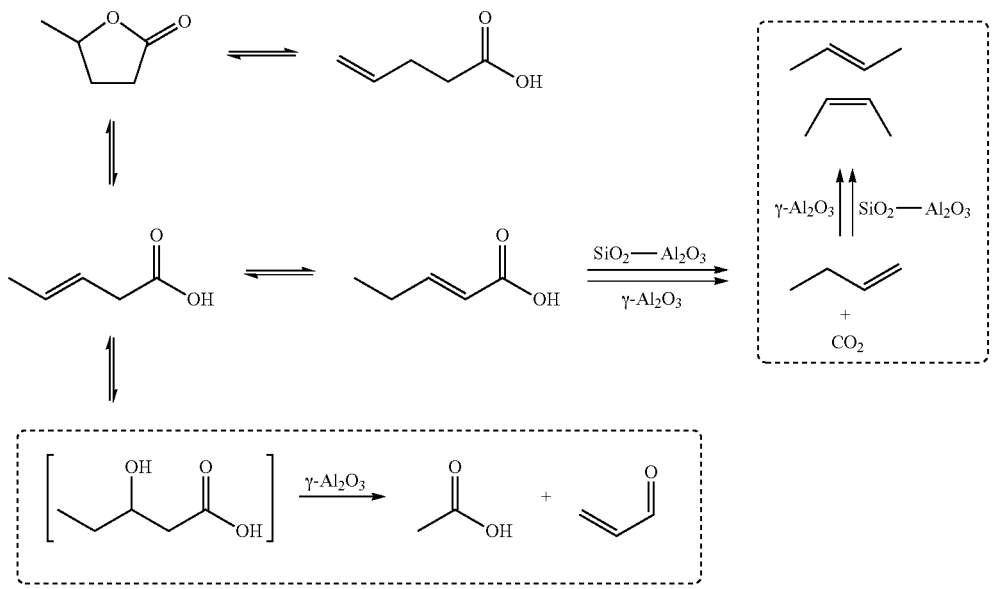

Scheme 1: Decarboxylation of γ-valeroactone (GVL)

2- and 3-pentenoic acids then irreversibly decarboxylates to form 1-butene and an equimolar amount of carbon dioxide, likely via a β-carbenium ion intermediate. J. Q. Bond, D. Wang, D. M. Alonso and J. A. Dumesic, *J. Catal.,* 2011, 281, 290-299. The 1-butene product then undergoes rapid isomerization over the $SiO_2$—$Al_2O_3$ catalyst to form trans- and cis-2-butene. Under typical operating conditions used to maximize the total butene yield from GVL (e.g., 30-60 wt % GVL in water, 648 K, 1 bar, WHSV=0.18-0.90 $h^{-1}$), J. Q. Bond, D. M. Alonso, D. Wang, R. M. West and J. A. Dumesic, *Science,* 2010, 327, 1110-1114, the isomerization of 1-butene essentially proceeds to equilibrium, and only 23% of the $C_4$ stream is retained as 1-butene. H. H. Voge and N. C. May, *J. Am. Chem. Soc.,* 1946, 68, 550-553. Therefore, it is challenging to produce 1-butene or other α-olefins selectively using the previously-studied solid Brønsted acid catalysts such as $SiO_2$—$Al_2O_3$, because these catalysts exhibit high activity for both formation of 1-butene and its isomerisation to 2-butene. Thus, in the present method, the decarboxylation of γ-lactones and/or the corresponding olefinic acids is coupled to a means to suppress the olefin isomerization reaction that converts the intermediate LAO into an internal olefin.

Using the present method, a stream of olefins containing unprecedentedly high levels of LAO was produced in a single flow reactor when a Lewis acid catalyst, such as γ-Al$_2$O$_3$ and the other Lewis acid catalysts listed above, were used to catalyze the decarboxylation of GVL, unsaturated acids or hydroxy carboxylic acids.

Catalyst Preparation:

γ-Al$_2$O$_3$ was obtained from STREM Chemicals (Newburyport, Mass.) and was pre-treated at 648 K in 60 cm$^3$ (STP) min$^{-1}$ helium (industrial grade; Airgas, Radnor, Pa.) for 3 hours before use. Amorphous SiO$_2$—Al$_2$O$_3$ was obtained from Grace Davison (Columbia, Md.) (SIAL 3113, Si/Al=3.40) and was pre-treated at 723 K in 100 cm$^3$ (STP) min$^{-1}$ air (Airgas, industrial grade) for 2 hours before use.

The tungstated alumina catalysts were prepared by incipient wetness impregnation of γ-Al$_2$O$_3$ with an aqueous solution of ammonium metatungstate (Sigma-Aldrich, St. Louis, Mo.; 99.99% trace metals basis). After impregnation, the material was dried at 383 K overnight followed by calcination at 723 K for 5 hours in static air. Before reaction studies, the catalysts were further pre-treated at 648 K in 60 cm$^3$ (STP) min$^{-1}$ helium (Airgas, industrial grade) for 3 hours. Catalyst containing 4 wt % WO$_3$ (calculated value) is denoted as 4WO$_x$—Al$_2$O$_3$.

The magnesium oxide (MgO) catalyst was obtained from NanoScale Materials, Inc. (Manhattan, Kans.) and was activated at 500K under 60 cm$^3$ (STP) min$^{-1}$ helium (Airgas, industrial grade) for 3 hours before reaction studies.

Catalytic Activity Measurements:

Reaction studies were conducted in 6.4 mm (0.25 inch, wall thickness=0.028 inch) outer diameter stainless steel tube. The reactor was packed with 100 mg~2 g of catalyst diluted with fine fused silica powder (Sigma-Aldrich). Two quartz wool plugs were used to seal both ends of the reactor. The reactor was heated by an insulated furnace (Applied Test Systems, Butler, A P; Series 3210), and temperature was monitored using a K type thermocouple (Omega Engineering Inc., Stamford, Conn.) and was controlled with a PID temperature controller (Love Controls, a division of Dwyer Instruments, Inc, Michigan City, Ind.; Series 16A). An HPLC pump (Alliance®-brand; Waters Corporation, Milford, Mass.) was used to deliver aqueous γ-valerolactone solution to the reactor. For γ-octalactone study, two syringe pumps were used to deliver water and γ-octalactone to the reactor due to the lower solubility of γ-octalactone in water. In the 1-butene isomerization study, 1-butene (Airgas, 5% in helium) was diluted with helium to obtain the targeted partial pressure needed in the feed. Gas flow was regulated using a mass flow controller (Brooks 5850 model), and the system pressure was maintained at 1 bar. The effluent liquid was collected in a gas-liquid separator maintained at room temperature and was drained periodically for analysis by HPLC or GC. The effluent gas was analyzed by two online GCs equipped with a flame ionization detector (Shimadzu model 2010) and a thermal conductivity detector (Shimadzu model GC-8A), respectively. Products were identified using a gas chromatograph/mass spectrometer system (Shimadzu GCQP-2010) and quantifications were performed using a gas chromatograph (Shimadzu GC-2010) equipped with flame ionization detector (Shimadzu Corporation, Kyoto, Japan). γ-Valerolactone, γ-octalactone, pentenoic acids, acetic acid, propionaldehyde, hexanaldehyde, octenoic acids and 1-heptene standards (Sigma-Aldrich) were used to obtain standard curves for analysis. Yields and conversions were defined as:

$$\text{Conversion} = \frac{\text{moles of lactones converted}}{\text{moles of lactones fed}}$$

$$\text{Selectivity} = \frac{\text{moles of product}}{\text{moles of lactones converted}}$$

$$\text{Yield} = \frac{\text{moles of product}}{\text{moles of lactones fed}}$$

Temperature-Programmed Desorption:

Temperature-programmed desorption of NH$_3$ or CO$_2$ was used to determine the total acid site density or total basic site density, respectively. 100-200 mg of catalyst was loaded in a glass flow-through cell. Before NH$_3$ or CO$_2$ adsorption, samples were treated at 648 K for 1 h under flowing helium (120 cm$^3$ (STP) min$^{-1}$) to remove adsorbed moisture. In the case of NH$_3$ adsorption, 1 mol % NH$_3$ in He (Airgas, 100 cm$^3$ (STP) min$^{-1}$) was then passed through the sample at 423 K for ca. 45 min. Physisorbed NH$_3$ was removed by holding the sample at 423 K under flow helium (120 cm$^3$ (STP) min$^{-1}$) for 45 min. In the case of CO$_2$ adsorption, 10 mol % CO$_2$ in He (Airgas, 100 cm$^3$ (STP) min$^{-1}$) was then passed through the sample at 298 K for ca. 45 min. Physisorbed CO$_2$ was removed by holding the sample at 298 K under flow helium (120 cm$^3$ (STP) min$^{-1}$) for 45 min. Temperature-programmed desorption was performed using a temperature ramp of 10 K min$^{-1}$ from room temperature to 1073 K under flowing He (50 cm$^3$ (STP) min$^{-1}$). The desorbed NH$_3$ or CO$_2$ was quantified by an online mass spectrometer (OmniStar-brand; Pfeiffer Vacuum, Asslar, Germany).

N$_2$ Adsorption:

Nitrogen adsorption-desorption isotherms were measured at 77 K using a Micromeritics (Norcross, Ga.) ASAP 2020 analyzer. The samples were degassed at 423 K for 5 hours prior to analysis. The specific surface areas of the materials were determined using the Brunauer-Emmett-Teller (BET) approach.

FTIR Spectroscopy of Adsorbed Pyridine:

The ratio of Brønsted and Lewis acid sites on the solid acid catalysts studied was determined from infrared spectroscopic measurements of adsorbed pyridine. Approximately 10 mg of catalyst was placed in a 1.2 cm die and pressed into a self-supporting wafer, which was placed in a treatment/sampling cell where it was heated to 648 K under flowing dry helium (Airgas, industrial grade) for 2 h. A reference spectrum of the catalyst was then taken. Pyridine was introduced into the cell through a bubbler for 30 min at room temperature, followed by purging under flowing helium for 1 h before another spectrum was taken. The areas of the pyridine peaks at 1455, and 1540 cm$^{-1}$, assigned to Lewis and Brønsted acid sites, respectively. C. A. Emeis, *J. Catal.* 1993, 141, 347-354, were determined by subtracting the spectra of the sample before and after pyridine exposure. The Brønsted/Lewis acid ratios were obtained by normalizing the areas with integrated molar extinction coefficients reported in the literature: 1.67 cm μmol$^{-1}$ for Brønsted sites and 2.22 cm μmol$^{-1}$ for Lewis sites. Id.

EXAMPLES

The following Examples are included to provide a more complete disclosure of the process claimed herein. The Examples are not intended to limit the scope of the claims in any fashion.

Example 1

In this working example of the present method, a γ-$Al_2O_3$ catalyst and a feedstock comprising GVL was used. Nearly pure 1-butene (>99% of $C_4$ stream) was obtained (10% total butene yield) under the operating conditions: 648K, 1 atm, WHSV (weight hourly space velocity) 1.83 $h^{-1}$ (see FIG. 2). γ-$Al_2O_3$ catalyst used in the examples was obtained from STREM Chemicals (Newburyport, Mass.) and was pre-treated at 648 K in 60 $cm^3$ (STP) $min^{-1}$ helium (industrial grade; Airgas, Radnor, Pa.) for 3 hours before use.

Example 2

In this working example of the present method, a γ-$Al_2O_3$ catalyst and a feedstock comprising GVL was used. High selectivity to 1-butene (>97% of $C_4$ stream) was obtained (34% total butene yield) under the operating conditions: 648K, 1 atm, WHSV (weight hourly space velocity) 0.37 $h^{-1}$ (see FIG. 2).

Example 3

In this working example of the present method, a γ-$Al_2O_3$ catalyst and a feedstock comprising GVL was used. The operating conditions were: 648K, 1 atm, WHSV (weight hourly space velocity) 0.18 $h^{-1}$ (see Table 1, Entry 2 and FIG. 2). The yield to total butenes can be increased at longer space time, which also leads to a slight decrease in percentage of 1-butene in the butene product stream. Under these conditions, over 92% selectivity to 1-butene was achieved at 43% total butene yield.

Example 4

In this working example of the present method, a γ-$Al_2O_3$ catalyst and a feedstock comprising GVL was used. The operating conditions were: 723K, 1 atm, WHSV (weight hourly space velocity) 1.83 $h^{-1}$ (see Table 1, row 3). The yield to total butenes can be increased at higher operational temperatures, which also leads to a decrease in percentage of 1-butene in the butene product stream. Under these conditions, over 82% selectivity to 1-butene was achieved at 59% total butene yield.

Example 5

In this working comparison, amorphous $SiO_2$—$Al_2O_3$ as a catalyst and a feedstock comprising GVL was used. The catalyst was obtained from Grace Davison (Columbia, Md.) (SIAL 3113, Si/Al=3.40) and was pre-treated at 723 K in 100 $cm^3$ (STP) $min^{-1}$ air (Airgas, industrial grade) for 2 hours before use. Under the operating conditions of 648K temperature, 1 bar pressure and WHSV of 21.6 $h^{-1}$, 92% of the product olefin stream can be retained as 1-butene using $SiO_2$—$Al_2O_3$ as the catalyst, but at a rather low 2% total butene yield (see FIG. 1). Thus it was observed with amorphous $SiO_2$—$Al_2O_3$ as a catalyst if a stream of highly pure 1-butene (e.g. >90%) is desired, the reactor needs to be operated at very low conversion levels. However, due to the high market demand, and hence high price of LAOs, the process is economically feasible, even at low conversion levels, due to the very high concentration (>90%) of LAO in the product stream. Once the 1-butene product is separated from unreacted lactone, the unreacted lactone may be recycled to the reactor inlet. In general, the LAO product is lighter than the corresponding lactone or olefinic acid reactant. Thus, the reactants are easily separated from the LAO product.

TABLE 1

Physiochemical properties and catalytic activities of solid catalysts for GVL (30 wt % in water) decarboxylation at 648 K, 1 bar.

| Entry | Catalyst | $CO_2$ uptake (μmol/g) | $BAS^c$/ LAS (μmol/g) | GVL conv (%) | $C^-_4$ $yield^d$ (%) | $AA^e$ yield (%) | $PEA^f$ yield (%) | 1-$C^-_4{}^g$ (%) |
|---|---|---|---|---|---|---|---|---|
| 1 | $SiO_2/Al_2O_3$ | <1 | 546/136 | 98 | 92 | <1 | 3 | 24.2 |
| 2 | γ-$Al_2O_3$ | 55 | 0/219 | 97 | 43 | 16 | 1 | 92.2 |
| 3 | γ-$Al_2O_3{}^a$ | 55 | 0/219 | 99 | 59 | 8 | 2 | 82.4 |
| 4 | 4W—$Al^b$ | 27 | 5/230 | 98 | 70 | 10 | 1 | 91.8 |
| 5 | 8W—Al | 10 | 32/191 | 96 | 73 | 8 | 3 | 71.0 |
| 6 | 20W—Al | 7 | 141/107 | 95 | 80 | 3 | 5 | 27.9 |
| 7 | MgO | 220 | — | 83 | 2 | 15 | 22 | 88.9 |

$^a$723 K.
$^b$denotes 4 wt % $WO_x$—$Al_2O_3$.
$^c$Brønsted acid sites/Lewis acid sites.
$^d$denotes butene.
$^e$denotes acetic acid.
$^f$denotes pentenoic acid.
$^g$1-butene percentage in total butenes.

Example 6

In this working comparison, amorphous $SiO_2$—$Al_2O_3$ as a catalyst and a feedstock comprising GVL was used. Under the operating conditions of 648K temperature, 1 bar pressure and WHSV of 1.83 $h^{-1}$, 72% of the product olefin stream can be retained as 1-butene using $SiO_2$—$Al_2O_3$ as the catalyst at 30% total butene yield (see FIG. 1).

Example 7

In this working comparison, amorphous $SiO_2$—$Al_2O_3$ as a catalyst and a feedstock comprising GVL was used. Under the operating conditions of 648K temperature, 1 bar pressure and WHSV of 0.18 $h^{-1}$, although high total butene yield of 90% was achieved, only 24% of the product olefin stream can be retained as 1-butene using $SiO_2$—$Al_2O_3$ as the catalyst (see FIG. 1). The predominant Brønsted acidity in $SiO_2$—$Al_2O_3$ catalyst that was previously found to afford the highest yield to total butene from GVL[8], showed much lower selectivity to 1-butene at high total butene yield. Given the trade-off between 1-butene selectivity and total butene yield over $SiO_2$—$Al_2O_3$, the maximum yield to 1-butene using $SiO_2$—$Al_2O_3$ as the catalyst is limited to approximately 22%.

Example 8

In this working example γ-$Al_2O_3$ modified with tungsten oxide ($WO_3$) as a catalyst and a feedstock comprising GVL was used. Tungstated alumina catalysts were prepared by incipient wetness impregnation of γ-$Al_2O_3$ with an aqueous solution of ammonium metatungstate (Sigma-Aldrich, St. Louis, Mo.; 99.99% trace metals basis). After impregnation, the material was dried at 383 K overnight followed by calcination at 723 K for 5 hours in static air. Before reaction studies, the catalysts were further pre-treated at 648 K in 60 $cm^3$ (STP) $min^{-1}$ helium (Airgas, industrial grade) for 3 hours. In this working example a catalyst containing 4 wt % $WO_3$ (calculated value) was used and is denoted as $4WO_x$—$Al_2O_3$. The physiochemical properties and catalytic activity of $4WO_x$—$Al_2O_3$ for butene production is presented in Table 1 (Entry 4). It can be seen from Table 1 that the loading of $WO_x$ on γ-$Al_2O_3$ creates Brønsted acidity at the expense of Lewis acidity, consistent with a previous report in S. L. Soled, G. B. McVicker, L. L. Murrell, L. G. Sherman, N. C. Dispenziere Jr, S. L. Hsu and D. Waldman, *J. Catal.*, 1988, 111, 286-295. The operating conditions were: 648K temperature, 1 bar pressure and WHSV of 0.09 $h^{-1}$. Remarkably, 4 wt % $WO_x$—$Al_2O_3$ catalyst is able to retain 92% of total $C_4$ olefin as 1-butene at total butene yield of 70%, leading to 64% yield to 1-butene.

Example 9

In this working example an 8 wt % $WO_3$ modified γ-$Al_2O_3$ (denoted as $8WO_x$—$Al_2O_3$) as a catalyst and a feedstock comprising GVL was used. The physiochemical properties and catalytic activity of $8WO_x$—$Al_2O_3$ for butene production is presented in Table 1 (Entry 5). The operating conditions were: 648K temperature, 1 bar pressure and WHSV of 0.09 $h^{-1}$. Using an 8 wt % $WO_x$—$Al_2O_3$ catalyst, 71% of total $C_4$ olefin as 1-butene at total butene yield of 73%, leading to 52% yield to 1-butene. Increasing the loading of $WO_x$ further from 4 to 8 wt % further created higher Brønsted acidity at the expense of Lewis acidity, as evident from a comparison of physiochemical properties of $4WO_x$—$Al_2O_3$ (Table 1, Entry 4) and $8WO_x$—$Al_2O_3$ (Table 1, Entry 5) and thus the selectivity of 1-butene decreases.

Example 10

In this working example a 20 wt % $WO_3$ modified γ-$Al_2O_3$ (denoted as $4WO_x$—$Al_2O_3$) as a catalyst and a feedstock comprising GVL was used. The physiochemical properties and catalytic activity of $20WO_x$—$Al_2O_3$ for butene production is presented in Table 1 (Entry 6). The operating conditions were: 648K temperature, 1 bar pressure and WHSV of 0.09 $h^{-1}$. Using an 20 wt % $WO_x$—$Al_2O_3$ catalyst, 27% of total $C_4$ olefin as 1-butene at total butene yield of 80%, leading to 22% yield to 1-butene. Thus, the catalytic behaviour of $WO_x$—$Al_2O_3$ with increasing $WO_x$ loading approaches that of $SiO_2$—$Al_2O_3$, whose activity is dominated by Brønsted acidity. This trend is clearly evidenced by the low 1-butene selectivity observed at high $WO_x$ loading of 20 wt % $WO_x$.

Example 11

Table 1 shows results using temperature programmed desorption of $CO_2$ to titrate basic sites on the various catalysts that were tested. The extent of $CO_2$ uptake is negligible for $SiO_2$—$Al_2O_3$. The $CO_2$ update for γ-$Al_2O_3$ is 55 µmol $CO_2$/g. Accordingly, the formation of acetic acid and propionaldehyde on the γ-$Al_2O_3$ catalyst as by-products (see process, Scheme 1) likely takes place by a retro-aldol type mechanism, which is known to be catalyzed by basic sites. R. Mahrwald, *Modern Aldol Reactions,* WILEY-VCH 2004. The decarboxylation of GVL over magnesium oxide (MgO), a basic oxide, was studied in this example. The magnesium oxide (MgO) catalyst was obtained from NanoScale Materials, Inc. (Manhattan, Kans.) and was activated at 500K under 60 $cm^3$ (STP) $min^{-1}$ helium (Airgas, industrial grade) for 3 hours before reaction studies. The MgO catalyst produced over seven times more acetic acid than butene from GVL conversion, implicating the importance of basic sites in this pathway. Importantly, the basic site density of γ-$Al_2O_3$ can be decreased by the progressive addition of $WO_x$ (0 to 20 wt %), leading to a corresponding decrease in the yields to acetic acid and condensation products (Table 1). In this respect, water-tolerant solid acid catalysts bearing predominantly Lewis acidity with minimal basicity are ideal for the selective production of LAOs via decarboxylation as described herein.

Example 12

In this working example we demonstrate that odd numbered LAOs can also be accessed by decarboxylation of starting lactones with even number of carbons by using $4WO_x$—$Al_2O_3$ catalyst and a feed comprising of γ-hexalactone (GHL). Under the operating conditions of 648K temperature, 1 bar pressure and WHSV of 1.93 $h^{-1}$, 97% of the product olefin stream can be retained as 1-pentene at 54% total pentene yield (see Table 2, Entry 1). Under the operating conditions of 648K temperature, 1 bar pressure and WHSV of 1.20 $h^{-1}$, 88% of the product olefin stream can be retained as 1-pentene at 61% total pentene yield (see Table 2, Entry 2).

Example 13

In this working example we demonstrate that higher LAOs can also be accessed by decarboxylation of lactones with longer carbon chains by using $4WO_x$—$Al_2O_3$ catalyst and a feed comprising of γ-octalactone (GOL). Under the operating conditions of 673K temperature, 1 bar pressure and WHSV of 7.0 $h^{-1}$, 97% of the product olefin stream can be retained as 1-heptene at 16% total heptene yield (see Table 2, Entry 3). Under the operating conditions of 673K temperature, 1 bar pressure and WHSV of 1.17 $h^{-1}$, 81% of the product olefin stream can be retained as 1-heptene at 58% total heptene yield (see Table 2, Entry 4).

TABLE 2

Production of high linear alpha olefins (LAOs) 4 wt % $WO_x$—$Al_2O_3$.

| Entry | Feed[a] | Lactone conv (%) | Olefin yield (%) | AA[d] yield (%) | Unsaturated acids yield (%) | LAO[e] (%) |
|---|---|---|---|---|---|---|
| 1 | 5 wt % GHL[b] | 82 | 54 | 8 | 12 | 97.1 |
| 2 | 5 wt % GHL[b] | 98 | 61 | 13 | 2 | 88.3 |
| 3 | 30 wt % GOL[c] | 91 | 16 | <1 | 58 | 96.5 |

TABLE 2-continued

Production of high linear alpha olefins (LAOs) 4 wt % $WO_x$—$Al_2O_3$.

| Entry | Feed[a] | Lactone conv (%) | Olefin yield (%) | AA[d] yield (%) | Unsaturated acids yield (%) | LAO[e] (%) |
|---|---|---|---|---|---|---|
| 4 | 10 wt % GOL[c] | 97 | 58 | 2 | 16 | 80.9 |
| 5 | 30 wt % GUL[c] | 88 | 7 | 4 | 56 | 96.8 |
| 6 | 10 wt % GUL[c] | 97 | 17 | 5 | 40 | 85.7 |

[a]co-fed with water using two syringe pumps.
[b]Reaction T = 648 K.
[c]Reaction T = 673 K.
[d]denotes acetic acid.
[e]LAO percentage in total olefins.

Example 14

In this working example we demonstrate that higher LAOs can also be accessed by decarboxylation of lactones with longer carbon chains by using $4WO_x$—$Al_2O_3$ catalyst and a feed comprising of γ-undecalactone (GUL). Under the operating conditions of 673K temperature, 1 bar pressure and WHSV of 3.54 $h^{-1}$, 97% of the product olefin stream can be retained as 1-decene at 7% total decene yield (see Table 2, Entry 5). Under the operating conditions of 673K temperature, 1 bar pressure and WHSV of 1.17 $h^{-1}$, 86% of the product olefin stream can be retained as 1-decene at 17% total decene yield (see Table 2, Entry 6). We observe that maintaining a high LAO percentage at a high total olefin yield becomes challenging with GUL (entries 5, 6), whereas a high 1-decene percentage can be obtained at lower total decene yield.

Example 15

This example demonstrates the further suppression of undesirable isomerization of the alpha-olefins over Lewis acid sites by co-feeding a solvent such as water. The isomerization is rapid over Brønsted acid sites, even in the presence of water. For example, the steady-state rates of 2-pentenoic acid decarboxylation and 1-butene isomerization over γ-$Al_2O_3$ are 0.012 (Feed: $P_{total}$=1 bar, $P_{PEA}$=0.07 bar, helium balance) and 0.15 mmol $min^{-1}$ $g_{cat}^{-1}$ ($P_{total}$=1 bar, $P_{1-butene}$=0.005 bar, helium balance), respectively. However, when water was co-fed, the decarboxylation rate increased to 0.051 ($P_{total}$=1 bar, $P_{PEA}$=0.07 bar, $P_{water}$=0.93 bar) while the 1-butene isomerization rate decreased to 0.020 mmol $min^{-1}$ $g_{cal}^{-1}$ ($P_{total}$=1 bar, $P_{1-butene}$=0.005 bar, 0.90 bar, helium balance). Under the same conditions, the rates of decarboxylation and 0.90 butene isomerization over $SiO_2$—$Al_2O_3$ without water are 0.48 and 8.78 mmol $min^{-1}$ $g_{cal}^{-1}$, respectively. When water was admitted into the system, the decarboxylation rate increased to 0.52 while the isomerization rate decreased only moderately to 4.50 mmol $min^{-1}$ $g_{cat}^{-1}$. Thus, in the exemplary reactions used here, adding water decreased the 1-butene isomerization rate by a factor of 7.5 over γ-$Al_2O_3$ and 1.9 over $SiO_2$—$Al_2O_3$. It is interesting (and unexpected) that γ-$Al_2O_3$ and $WO_x$—$Al_2O_3$ can be used to selectively produce LAOs because both catalysts are known to have good activity for olefin double bond migration and skeletal isomerization at temperatures similar to those used in the present study (673~800 K). L. H. Gielgens, M. G. H. Vankampen, M. M. Broek, R. Vanhardeveld and V. Ponec, *J. Catal.*, 1995, 154, 201-207. This development thus represents an interesting case where the high water content commonly encountered in biomass processing can be utilized to influence product selectivity positively.

In summary, disclosed and demonstrated herein is a method to produce a stream of highly pure LAOs from lactones or unsaturated carboxylic acids in a single step using inexpensive, robust heterogeneous acid catalysts with no precious metal components. Analogous decarboxylation chemistry has been shown for $C_5$, $C_6$, $C_8$ and $C_{11}$ γ-lactones, which indicates that the method is a general approach for producing LAOs with varying chain lengths. The feedstock to this process can be derived from biological routes (e.g., polyketide/fatty acid biosynthesis) and/or from biomass, which thereby generates a series of homologous molecules for conversion to LAOs. Moreover, unlike the present ethylene-based route for production of LAOs, this new biological route is capable of targeting molecules with specified carbon chain length which after subsequent decarboxylation with the current technology, leads to a single LAO cut, thus offering additional manufacturing flexibility to meet market demand. This approach also allows for the production of even and odd carbon-number LAOs, depending on the number of carbons in the starting molecules. Such an integrated approach demonstrates the promise of a synergy between biocatalysis and chemical catalysis for efficiently converting biomass into value-added chemicals.

What is claimed is:

1. A method to make linear alpha olefins comprising:
   a) contacting in a reactor a feedstock comprising a component selected from the group consisting of at least one lactone, at least one unsaturated carboxylic acid, at least one hydroxy carboxylic acid, and a combination thereof, with a solid acid catalyst having acidic catalytic sites, wherein the acidic catalytic sites include Lewis acid catalytic sites, for a time and a temperature wherein at least a fraction of the component is converted into linear alpha olefins; and
   b) removing the linear alpha olefins from the solid acid catalyst by flowing an inert gas through the reactor, thereby minimizing isomerization of the linear alpha olefins to internal olefins;
   wherein the solid acid catalyst is selected from the croup consisting of γ-$Al_2O_3$, ≤8 wt % $WO_x$ supported on γ-$Al_2O_3$ and MgO; and
   wherein the linear alpha olefins comprise at least 71.0 mol % of all olefins formed in the method.

2. The method of claim 1, further comprising contacting the feedstock with the solid acid catalyst in the presence of a co-solvent.

3. The method of claim 2, wherein the co-solvent is water.

4. The method of claim 1, wherein at least 50% of the acidic catalytic sites on the solid acid catalyst are Lewis acid catalytic sites.

5. The method of claim 4, further comprising contacting the feedstock with the solid acid catalyst in the presence of a co-solvent.

6. The method of claim 5, wherein the co-solvent is water.

7. The method of claim 1, wherein at least 60% of the acidic catalytic sites on the solid acid catalyst are Lewis acid catalytic sites.

8. The method of claim 7, further comprising contacting the feedstock with the solid acid catalyst in the presence of a co-solvent.

9. The method of claim 8, wherein the co-solvent is water.

10. The method of claim 1, wherein at least 70% of the acidic catalytic sites on the solid acid catalyst are Lewis acid catalytic sites.

11. The method of claim 10, further comprising contacting the feedstock with the solid acid catalyst in the presence of a co-solvent.

12. The method of claim 11, wherein the co-solvent is water.

13. The method of claim 1, wherein at least 80% of the acidic catalytic sites on the solid acid catalyst are Lewis acid catalytic sites.

14. The method of claim 13, further comprising contacting the feedstock with the solid acid catalyst in the presence of a co-solvent.

15. The method of claim 14, wherein the co-solvent is water.

16. The method of claim 1, wherein at least 90% of the acidic catalytic sites on the solid acid catalyst are Lewis acid catalytic sites.

17. The method of claim 16, further comprising contacting the feedstock with the solid acid catalyst in the presence of a co-solvent.

18. The method of claim 17, wherein the co-solvent is water.

19. The method of claim 1, comprising contacting the feedstock with the solid acid catalyst at a temperature of from 500 K to 1000 K.

20. The method of claim 19, further comprising contacting the feedstock with the solid acid catalyst in the presence of a co-solvent.

21. The method of claim 20, wherein the co-solvent is water.

22. The method of claim 1, comprising contacting the feedstock with the solid acid catalyst at a temperature of from 600 K to 900 K.

23. The method of claim 22, further comprising contacting the feedstock with the solid acid catalyst in the presence of a co-solvent.

24. The method of claim 23, wherein the co-solvent is water.

25. The method of claim 1, comprising contacting the feedstock with the solid acid catalyst at a temperature of from 625 K to 850 K.

26. The method of claim 25, further comprising contacting the feedstock with the solid acid catalyst in the presence of a co-solvent.

27. The method of claim 26, wherein the co-solvent is water.

28. The method of claim 1, comprising contacting the feedstock with the solid acid catalyst at a temperature of from 650 K to 800 K.

29. The method of claim 28, further comprising contacting the feedstock with the solid acid catalyst in the presence of a co-solvent.

30. The method of claim 29, wherein the co-solvent is water.

31. The method of claim 1, wherein the solid acid catalyst is $\gamma$-$Al_2O_3$.

32. The method of claim 1, wherein the linear alpha olefins comprise at least 82.4 mol % of all olefins formed in the method.

33. The method of claim 1, wherein the linear alpha olefins comprise at least 92.2 mol % of all olefins formed in the method.

34. The method of claim 1, wherein the linear alpha olefins comprise at least 97.0 mol % of all olefins formed in the method.

* * * * *